United States Patent
Larsen et al.

(10) Patent No.: US 12,245,986 B2
(45) Date of Patent: Mar. 11, 2025

(54) DEVICE FOR FORMING A MEDICAL PASTE

(71) Applicant: Ferrosan Medical Devices A/S, Søborg (DK)

(72) Inventors: Kristian Larsen, Værløse (DK); Peter Lund Hammershøj, Brønshøj (DK)

(73) Assignee: Ferrosan Medical Devices A/S, Søborg (DK)

(*) Notice: Subject to any disclaimer, the term of this patent is extended or adjusted under 35 U.S.C. 154(b) by 0 days.

(21) Appl. No.: 18/491,072

(22) Filed: Oct. 20, 2023

(65) Prior Publication Data

US 2024/0041699 A1 Feb. 8, 2024

Related U.S. Application Data

(63) Continuation of application No. 17/056,560, filed as application No. PCT/EP2019/067018 on Jun. 26, 2019, now Pat. No. 11,865,077.

(30) Foreign Application Priority Data

Jun. 27, 2018 (EP) .................................... 18180033

(51) Int. Cl.
*A61J 1/20* (2006.01)
*A61B 17/00* (2006.01)
(Continued)

(52) U.S. Cl.
CPC ....... *A61J 1/2096* (2013.01); *A61B 17/00491* (2013.01); *A61J 1/06* (2013.01);
(Continued)

(58) Field of Classification Search
CPC .. A61J 1/00; A61J 1/2096; A61J 1/201; A61J 1/2017; A61J 1/2048; A61J 1/2082;
(Continued)

(56) References Cited

U.S. PATENT DOCUMENTS 3,548,825 A 12/1970 Shaw
11,865,077 B2 1/2024 Larsen et al.
(Continued)

FOREIGN PATENT DOCUMENTS

CN 107580489 A 1/2018
WO 2006120461 A1 11/2006
(Continued)

OTHER PUBLICATIONS

International Search Report, issued in international application No. PCT/EP2019/067018, entitled "Device for Forming a Medical Paste", Date of Mailing: Aug. 6, 2019.
(Continued)

*Primary Examiner* — John Kim
(74) *Attorney, Agent, or Firm* — Hamilton, Brook, Smith & Reynolds, P.C.

(57) ABSTRACT

A device for reconstituting a bioactive agent and forming a flowable paste is described. The device comprises a base configured for receiving: a first container containing a liquid, and a second container containing the bioactive agent, a syringe containing a paste forming material, the syringe being attachable to the base, wherein the base has a first conduit for fluidly connecting the first container with the second container and a second conduit for fluidly connecting the second container with the syringe, and wherein the first container is configured to be pressurizable such that when the first and second containers are received at the base, the liquid is forced through the first conduit into the second container, thereby reconstituting the bioactive agent, and the reconstituted bioactive agent is forced through the second conduit into the syringe, such that a paste is formed.

18 Claims, 6 Drawing Sheets

(51) Int. Cl.
*A61J 1/06* (2006.01)
*A61M 5/162* (2006.01)
*A61M 5/178* (2006.01)
*A61M 5/19* (2006.01)
*A61M 5/20* (2006.01)
*A61M 5/24* (2006.01)
*A61M 35/00* (2006.01)
*A61M 39/00* (2006.01)

(52) U.S. Cl.
CPC ............. *A61J 1/201* (2015.05); *A61J 1/2017* (2015.05); *A61J 1/2048* (2015.05); *A61J 1/2082* (2015.05); *A61J 1/2089* (2013.01); *A61M 5/162* (2013.01); *A61M 5/1782* (2013.01); *A61M 5/19* (2013.01); *A61M 5/2046* (2013.01); *A61M 5/2053* (2013.01); *A61M 5/2425* (2013.01); *A61M 5/2448* (2013.01); *A61M 35/003* (2013.01); *A61B 2017/00495* (2013.01); *A61M 2039/0027* (2013.01)

(58) Field of Classification Search
CPC ............ A61J 1/2089; A61J 1/06; A61M 5/19; A61M 5/2053; A61M 5/2448; A61M 5/162; A61M 5/1782; A61M 5/2046; A61M 5/2425; A61M 35/003; A61M 2039/0027; A61B 17/00491; A61B 2017/00495
See application file for complete search history.

(56) References Cited

U.S. PATENT DOCUMENTS

| | | |
|---|---|---|
| 2002/0004643 A1 | 1/2002 | Carmel et al. |
| 2009/0099547 A1 | 4/2009 | Radmer |
| 2012/0089088 A1 | 4/2012 | Foshee et al. |
| 2013/0046270 A1 | 2/2013 | Foshee et al. |
| 2021/0244616 A1 | 8/2021 | Larsen et al. |

FOREIGN PATENT DOCUMENTS

| | | |
|---|---|---|
| WO | 2007122209 A1 | 11/2007 |
| WO | 2007147741 A1 | 12/2007 |
| WO | 2009146088 A1 | 12/2009 |
| WO | 2010043685 A1 | 4/2010 |
| WO | 2016154413 A1 | 9/2016 |

OTHER PUBLICATIONS

Written Opinion, issued in international application No. PCT/EP2019/067018, entitled "Device for Forming a Medical Paste", Date of Mailing: Aug. 6, 2019.

International Preliminary Report on Patentability, issued in PCT/EP2019/067018, entitled "Device for Forming a Medical Paste", Date of Mailing: Aug. 4, 2020.

Notice of Allowance and Fee(s) Due, issued on Aug. 23, 2023, for U.S. Appl. No. 17/056,560, entitled "Device for Forming a Medical Paste,".

DEVICE FOR FORMING A MEDICAL PASTE

RELATED APPLICATIONS

This application is a continuation of U.S. application Ser. No. 17/056,560, filed Nov. 18, 2020, now U.S. Pat. No. 11,865,077, issued on Jan. 9, 2024, which is the U.S. National Stage of International Application No. PCT/EP2019/067018, filed on Jun. 26, 2019, published in English, which claims priority under 35 U.S.C. § 119 or 365 to EP Application No. 18180033.5, filed Jun. 27, 2018. The entire teachings of the above application(s) are incorporated herein by reference.

FIELD OF INVENTION

The present invention relates to a device, a kit of parts, and a method for forming a medical paste, such as a device and method for reconstituting a bioactive agent and for forming a flowable paste in a syringe.

BACKGROUND OF INVENTION

A paste may be precisely applied to a target site by use of a syringe. A syringe comprises a plunger, or piston, fitted to a barrel with an opening, where the barrel comprises the paste. By pushing or translating the syringe plunger along the barrel, the paste being in the form of an essentially non-compressible thick viscous composition, is discharged from the opening of the syringe barrel in a controlled manner. Thus, a paste may be delivered to a target site with high spatial precision and in a flexible dosage, by use of a syringe.

The delivery of a paste to a specific target site and in a precise amount, is essential for pastes, which are applied for medical purposes, such as for surgical applications. For example, haemostatic compositions for surgical applications are typically in the form of a paste.

An example of an effective surgical haemostat is a gelatine paste comprising a haemostatically effective amount of thrombin. Thrombin is a clotting agent, and may thus be used to control the bleeding at a haemorrhaging site. However, for the medical paste to be haemostatically efficient, it is essential that an effective concentration of the thrombin is present in the paste, that the thrombin is uniformly distributed in the paste, and that the paste has a suitable viscosity and rheology for precise and fixed positioning.

Thus, to obtain an efficient medical paste, the step of manufacturing the paste with sufficient uniform distribution of the agents, as well as correct concentration of the bioactive agent, and correct ratio between the components, is essential.

The efficiency of the paste will also depend on the paste storage time after preparation, since the paste consistency or rheology may degrade over time, and also the efficiency of the bioactive agent may degrade over time due to chemical instability. For most bioactive agents, the storage stable form is the dry state, and storage in a paste or other liquid states are usually not storage stable forms. The dry bioactive agent may be reconstituted to a liquid form by mixing with a liquid.

To ensure the quality and efficiency of the paste, medical pastes are typically prepared on-site and immediately prior to use. The on-site preparation demands high precision of the person preparing the paste, who typically is under time pressure during the surgical procedure. Thus, the step of preparing the paste involves a risk of incorrect concentration dosages of the bioactive agent, and insufficient mixing of the paste.

Mixing procedures and manipulations of different substances can be time consuming.

In an Operation Room (OR) setting this time consumption may be critical when using a haemostatic paste for inhibiting bleedings as the surgeon will have to interrupt his procedure while waiting for the haemostat. Thus, the preparation time of the paste may cause increased blood loss and longer operating time of the surgical procedure.

Mixing substances from different containers may also potentially compromise the sterility of the haemostatic paste and can negatively affect the consistency of the haemostatic paste if not done correctly. A correct paste consistency is important for a satisfactory haemostatic effect.

To minimize the risk of erroneously mixed pastes, and the associated waste of bioactive agent and inefficient treatment of the patient, and to reduce the paste preparation time, there is a need for a paste preparation that is more efficient, such as includes partly or fully automated steps.

WO 10/043685 [1] discloses a device for mixing two substances, such as an active powdered drug and a diluent. The two substances are initially stored in two separate compartments, and they are mixed upon generating a fluid flow between the two compartments. The driving force for generating the fluid flow may be a pre-established positive pressure in the first container. Thus, an exact diluent to drug ratio is obtained in the mixed product. The mixed material may be retrieved to a syringe, and administered to the body by e.g. injection or infusion.

Despite the advances in the field, there is a need for more simple, efficient, and reliable devices and methods for preparing medical mixtures, such as medical pastes.

SUMMARY OF INVENTION

The present invention provides a device, a kit of parts, and a method for a more simple, efficient, and reliable preparation of a medical paste. Advantageously, the medical paste is produced directly in a syringe. Thus, for example the device and method may be used for fast, easy, convenient, and reliable reconstitution of a bioactive agent, such as a lyophilized drug, with a liquid or diluent, and a paste forming material, usually in the form of a biocompatible polymer, to form a flowable haemostatic matrix for use in surgical procedures. Thus, the device and process may result in improved surgical procedures, including limited blood loss and lower operating time of the surgical procedures.

The present invention is surprisingly suitable for the incorporation of thrombin in haemostatic pastes, and facilitates that a haemostatic paste comprising thrombin may be generated in a single step operation. Such simple and fast method for preparing a haemostatic composition is highly valuable in the operating room where potential bleeding must be controlled in a fast and efficient manner.

A first aspect of the invention relates to a device for reconstituting a bioactive agent and forming a paste, the device comprising:
 a base configured for receiving:
 a first container containing a liquid, and
 a second container containing the bioactive agent,
 a syringe containing a paste forming material, the syringe being attachable to the base.

The base preferably has a first conduit for fluidly connecting the first container with the second container and a second conduit for fluidly connecting the second container with the syringe.

Advantageously the first container is configured to be pressurizable such that when the first and second containers are received at the base, the liquid is forced through the first conduit into the second container, thereby reconstituting the bioactive agent, and the reconstituted bioactive agent is forced through the second conduit into the syringe, such that a paste is formed.

Further advantageously, the first container is pressurized by liquid pressure, or by compression, optionally elastic deformation, of the container.

In a preferred embodiment, the paste is formed directly in the syringe. In a further preferred embodiment the paste is flowable.

A second aspect of the invention relates to a kit of parts for the device according to the first aspect, comprising a base, a syringe containing a paste forming material, a first container containing a liquid, and a second container containing a bioactive agent.

A third aspect of the invention relates to a method for reconstituting a bioactive agent and forming a paste, the method comprising:

- providing a first container containing a liquid under positive pressure,
- providing a second container containing the bioactive agent,
- providing a syringe containing a paste forming material.

Preferably fluidly connecting the first container with the second container and fluidly connecting the second container with the syringe such that the liquid is forced from the first container into the second container, thereby reconstituting the bioactive agent, and the reconstituted bioactive agent is forced from the second container into the syringe, such that a paste is formed.

A fourth aspect of the invention relates to a method according to the third aspect, configured to be carried out using the device according to the first aspect or the kit according to the second aspect.

A fifth aspect of the invention relates to use of the device according to the first aspect or the kit according to the second aspect for the method according to the third aspect.

DESCRIPTION OF DRAWINGS

The invention will in the following be described in greater detail with reference to the accompanying drawings.

FIG. 1 shows an embodiment of the device according to the present disclosure for reconstituting a bioactive agent and forming a flowable paste in a syringe, where the first container is pressurized by liquid pressure. The device of FIG. 1 is shown in a configuration before the first and second containers are received at the base, and the connections to the base conduits are formed.

FIG. 2 shows an embodiment of the device of FIG. 1, when the first and second containers are received at the base and the connections to the conduits are formed.

FIG. 3 shows an embodiment of the device of FIGS. 1-2, when the liquid of the first container has been uniformly mixed with the bioactive agent to form a reconstituted agent 4*c*.

FIG. 4 shows an embodiment of the device of FIGS. 1-3, when the reconstituted bioactive agent has been uniformly mixed with the paste forming material pre-loaded in the syringe, thereby forming a flowable paste 5*c* in the syringe.

FIG. 5 shows an embodiment of a syringe including a flowable paste, which has been detached from the base, and which is ready for discharging the paste at a target site.

FIG. 6 shows an embodiment of a kit of parts for assembling the device of FIGS. 1-4.

FIG. 7 shows an embodiment of the device according to the present disclosure for reconstituting a bioactive agent and forming a flowable paste in a syringe, where the first container is pressurized by elastic deformation. (A) shows the configuration before the first and second containers are received at the base, and the connections to the base conduits are formed. (B) shows the configuration when the first and second containers are received at the base and the connections to the conduits are formed.

DETAILED DESCRIPTION OF THE INVENTION

The invention is described below with the help of the accompanying figures. It would be appreciated by the people skilled in the art that the same feature of component of the device are referred with the same reference numeral in different figures. A list of the reference numbers can be found at the end of the detailed description section.

The present disclosure relates to a device, a kit, and a method for forming a medical paste directly in a syringe. Subsequently, the medical paste may be discharged from the syringe, and delivered to a target site with high spatial precision and in a flexible dosage.

More specifically, the present disclosure relates to a device, a kit, and a method for forming a medical paste spontaneously and automatically in a syringe. The medical paste is formed spontaneously when the containers are received at the base. Thus, the medical paste may be generated in a single step operation, where the single step is an initiation step, such as the assembly and receival at the base.

Driving Force

The term "spontaneous" is used to describe phenomena arising from internal forces or causes, which are independent of external agencies or stimuli and which happen within a short period of time, i.e. preferably within less than about 30 seconds, more preferred within less than about 20 seconds, even more preferred within less than about 10 seconds or within less than about 5 seconds, such as within less than about 3 seconds, for example less than about 2 seconds.

The spontaneous formation of the paste is triggered by a container configured to be pressurizable. A pressurized container may be characterized as having pressure energy stored, where the pressure energy may be converted to kinetic energy by releasing the pressure, e.g. upon manually opening the container, or piercing the container. The pressurized container may contain a fluid, and the fluid is discharged from the container simultaneously as the pressure is released, as is known from pressurized beverages.

When the discharged fluid is released into a second container, the discharged fluid will be mixed with the materials of the second container due to the released kinetic energy and turbulent flow. However, the degree of mixing, and thus the uniformity of the resulting mixture, will depend on the pressure energy, the viscosity of the discharged fluid, and the viscosity of the material in the second container. The higher the viscosity of the second container material, the more energy is needed for producing a uniform mixture.

If the discharged fluid is a liquid, and the second container material is a fluid, a low amount of energy is needed for forming a uniform mixture between the two fluids. If on the other hand the the discharged fluid is a liquid and the second container material is a paste, more energy is needed for forming a uniform mixture between the fluid and the paste component. The second container material may also be a solid, such as particles of powder. In this case, the fluid solubility and/or the ability of the fluid to suspend the solid particles, in addition to the kinetic energy, will affect the ability to form a uniform mixture between the solid and the discharged fluid.

It was surprisingly found that sufficient reconstitution of a bioactive agent, and further sufficient mixing of the reconstituted agent to form a uniform paste may be obtained with the kit and device according to the present disclosure, where the paste is generated in a single step operation. Thus, the device provides a self-containing system for spontaneously forming a medical paste in a single step operation.

Medical Paste

Advantageously, the device and kit according to the present disclosure is applied for producing and mixing a medical paste. By the term "medical paste" is meant a paste comprising a bioactive agent. An example of a bioactive agent is thrombin.

A "bioactive agent" is defined as any agent, drug, compound, composition of matter or mixture which provides some pharmacologic, often beneficial, effect that can be demonstrated in vivo or in vitro. An agent is thus considered bioactive if it has interaction with or effect on a cell tissue in the human or animal body. As used herein, this term further includes any physiologically or pharmacologically active substance that produces a localized or systemic effect in an individual. Bioactive agents may be a protein, such as an enzyme. Further examples of bioactive agents include, but are not limited to, agents comprising or consisting of an oligosaccharide, a polysaccharide, an optionally glycosylated peptide, an optionally glycosylated polypeptide, an oligonucleotide, a polynucleotide, a lipid, a fatty acid, a fatty acid ester and secondary metabolites. It may be used either prophylactically, therapeutically, in connection with treatment of an individual, such as a human or any other animal. The term "bioactive agent" as used herein does not encompass cells, such as eukaryotic or prokaryotic cells.

A "paste" according to the present disclosure has a malleable, putty-like consistency, such as toothpaste. A paste is a thick fluid mixture of pulverized solid/solid in powder form with a liquid. A paste is a substance that behaves as a solid until a sufficiently large load or stress is applied, at which point it flows like a fluid, i.e. a paste is flowable. Flowables conform efficiently to irregular surfaces upon application. Pastes typically consist of a suspension of granular material in a background fluid. The individual grains are jammed together like sand on a beach, forming a disordered, glassy or amorphous structure, and giving pastes their solid-like character. It is this "jamming together" that gives pastes some of their most unusual properties; this causes a paste to demonstrate properties of fragile matter. A paste is not a gel/jelly. A "slurry" is a fluid mixture of a powdered/pulverized solid with a liquid, such as water. Slurries behave in some ways like thick fluids, flowing under gravity and being capable of being pumped if not too thick. A slurry may functionally be regarded as a thin, watery paste, but a slurry generally contains more water than a paste. Substantially water-insoluble powder particles, such as cross-linked gelatine particles, will form a paste upon mixing with an aqueous medium.

A "gel" is a solid, jelly-like material that can have properties ranging from soft and weak to hard and tough. Gels are defined as a substantially dilute cross-linked system, which exhibits no flow when in the steady-state. By weight, gels are mostly liquid, yet they behave like solids due to a three-dimensional cross-linked network within the liquid. It is the crosslinks within the fluid that give a gel its structure (hardness) and contribute to stickiness (tack). In this way gels are a dispersion of molecules of a liquid within a solid in which the solid is the continuous phase and the liquid is the discontinuous phase. A gel is not a paste or slurry. For example, non-crosslinked gelatine is soluble and forms a gel upon contact with an aqueous medium such as water.

For a medical paste to be discharged from a syringe, it should be flowable when subjected to a force applicable for a syringe. Thus, by the term "flowable paste" is meant a paste having a viscosity facilitating a steady flow, when subjected to a force applicable for a syringe. An example of a flowable paste is a paste having a viscosity between 500-3500 Pa·s, when measured at 30° C. and a relative humidity between 65-75%.

In an embodiment of the disclosure, the paste is flowable.

Forming a medical paste, such as a flowable medical paste, requires mixing of the bioactive agent with a paste or a paste forming material. Typically, bioactive agents are stored in a solid and dried state, such as a powdered form, facilitating stable storage of the active agent, and flexible concentrations by mixing the bioactive agent with a diluent in an adjustable ratio. Thus, for the bioactive agent to be administered by a syringe injection, the solid bioactive agent must first be reconstituted. Forming a medical paste therefore typically requires the steps of mixing a solid bioactive agent with a liquid or diluent to reconstitute the bioactive agent, and subsequently mixing the reconstituted bioactive agent with a paste forming material, which may also be referred to as a "paste precursor".

By the term "paste forming material" is meant a material for forming a paste from a liquid phase, such as a reconstituted bioactive agent. Thus, a paste forming material may also be referred to as a precursor material for forming a paste.

The reconstituted bioactive agent is obtained by mixing the bioactive agent with a liquid with low viscosity, such as sterile water or saline water, thereby ensuring uniform reconstitution. Thus, the reconstituted bioactive agent is a liquid with low viscosity. A paste may be obtained from the reconstituted bioactive agent by adding a paste forming material, which inherently increases the viscosity.

Mixing Device

Figure 1:
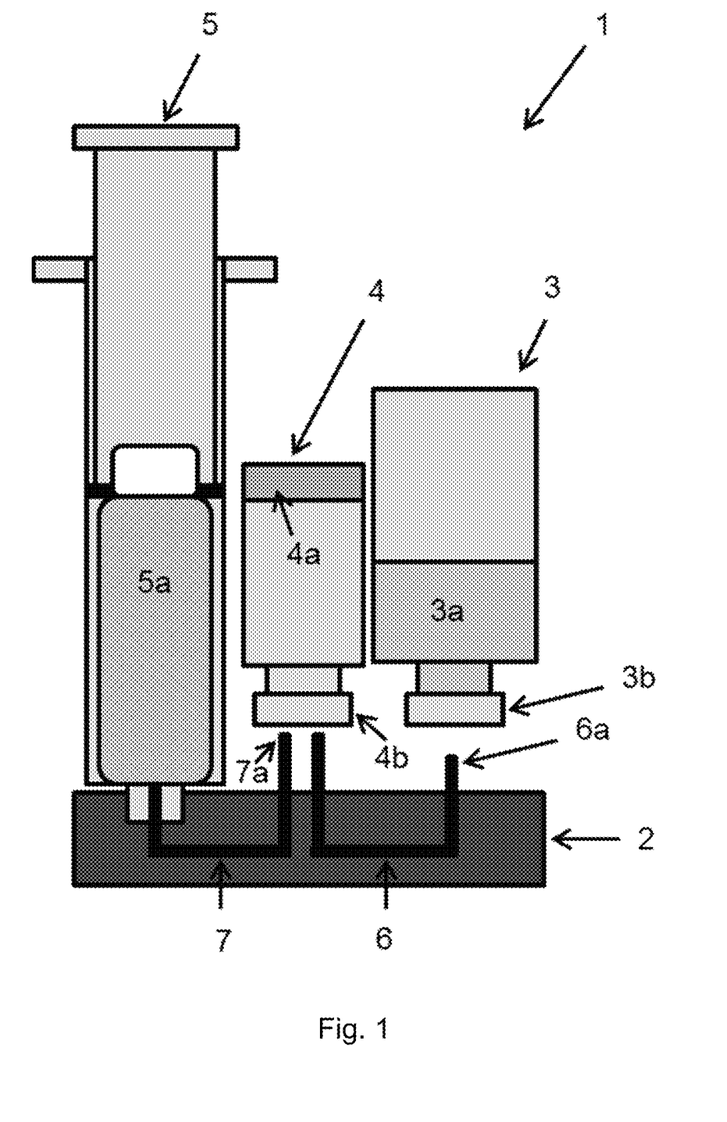

The present disclosure relates to a novel way of reconstituting a bioactive agent and forming a flowable paste in a syringe. FIG. 1 shows an embodiment of the device for the purpose, prior to the initiating step and initiating the reconstitution process. The device 1 comprises a base 2 and a syringe 5. The syringe is detachably attached to the base e.g. by a locking mechanism, and the syringe is further pre-loaded with a paste forming material 5a. For example, the syringe may be mounted in the base station by a threaded screwing mechanism, prior to initiating the reconstitution process.

The base is configured for receiving two containers: a first container 3 containing a liquid 3a, and a second container 4 containing a bioactive agent 4a. A typically bioactive agent is supplied in a solid and dry state, and the bioactive agent may therefore at least partly adhere to the bottom of the container as illustrated in FIG. 1. The base of FIG. 1 further comprises two conduits: a first conduit 6 and a second conduit 7, configured such that when the first and second containers are received at the base, the first conduit forms a fluid connection between the first container and the second container, and the second conduit forms a fluid connection between the second container and the syringe. Thus, when the first and second containers are received at the base, the connections to the conduits are formed.

The first container of FIG. 1 is configured to be pressurizable, and thereby containing a positive pressure, such that when the first and second containers are received at the base and the connection to the conduit is formed, the positive pressure forces the liquid out of the first container, through the first conduit, and into the second container. The liquid forced by the positive pressure will further provide turbulent flow within the second container, and thus ensure that the liquid and bioactive agent is uniformly mixed within the second container, thereby forming a reconstituted active agent.

Figure 2:
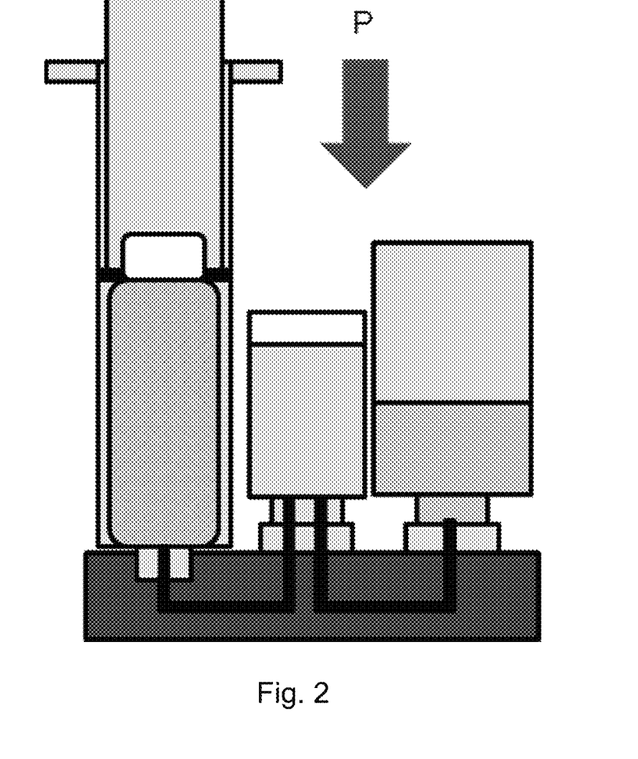
Figure 3:
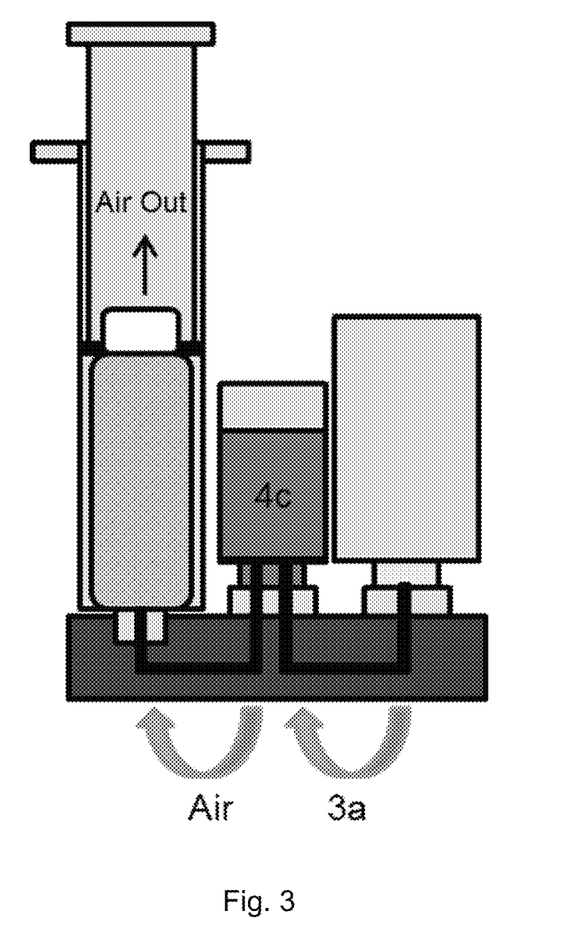

FIG. 2 shows an embodiment of the device, when the first and second containers are received at the base and the connections to the conduits are formed. The initiaing step resulting in the receival at the base may be obtained by applying a manual pressure as indicated in FIG. 2. The containers are pushed manually in a direction towards the base, such that an opening of the first container 3b and an opening of the second container 4b is brough into contact with the conduits. FIG. 3 shows the embodiment, when the liquid of the first container 3a has been uniformly mixed with the bioactive agent to form a reconstituted bioactive agent 4c.

Figure 4:
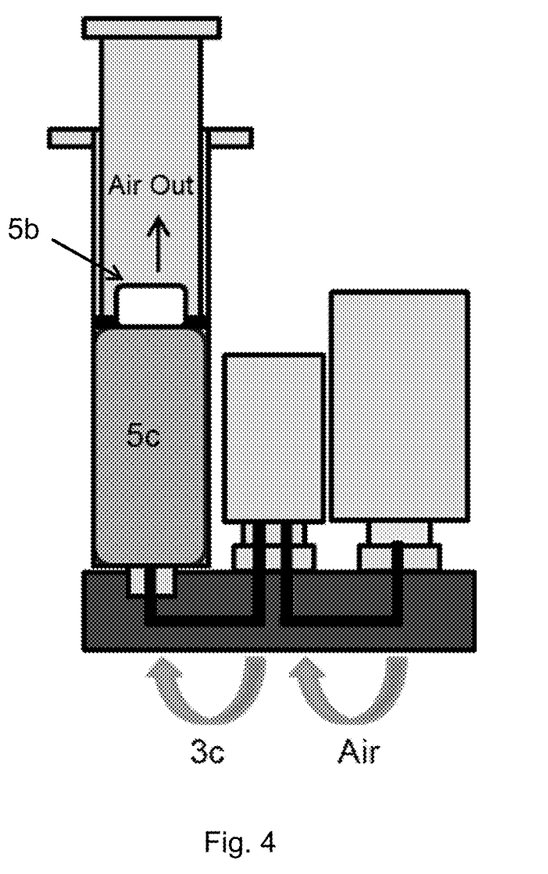

Since the second container, conduits, and syringe of the device have a fixed volume and are non-compressible elements, the positive pressure of the first container will further force the reconstituted bioactive agent 4c out of the second container, through the second conduit, and into the syringe, as illustrated in FIG. 4. The reconstituted bioactive agent, which is forced by the positive pressure, will further provide turbulent flow within the syringe, and thus ensure that the reconstituted bioactive agent is uniformly mixed with the paste forming material pre-loaded in the syringe. Thus a flowable paste 5c is formed in the syringe as illustrated in FIG. 4.

Figure 7:
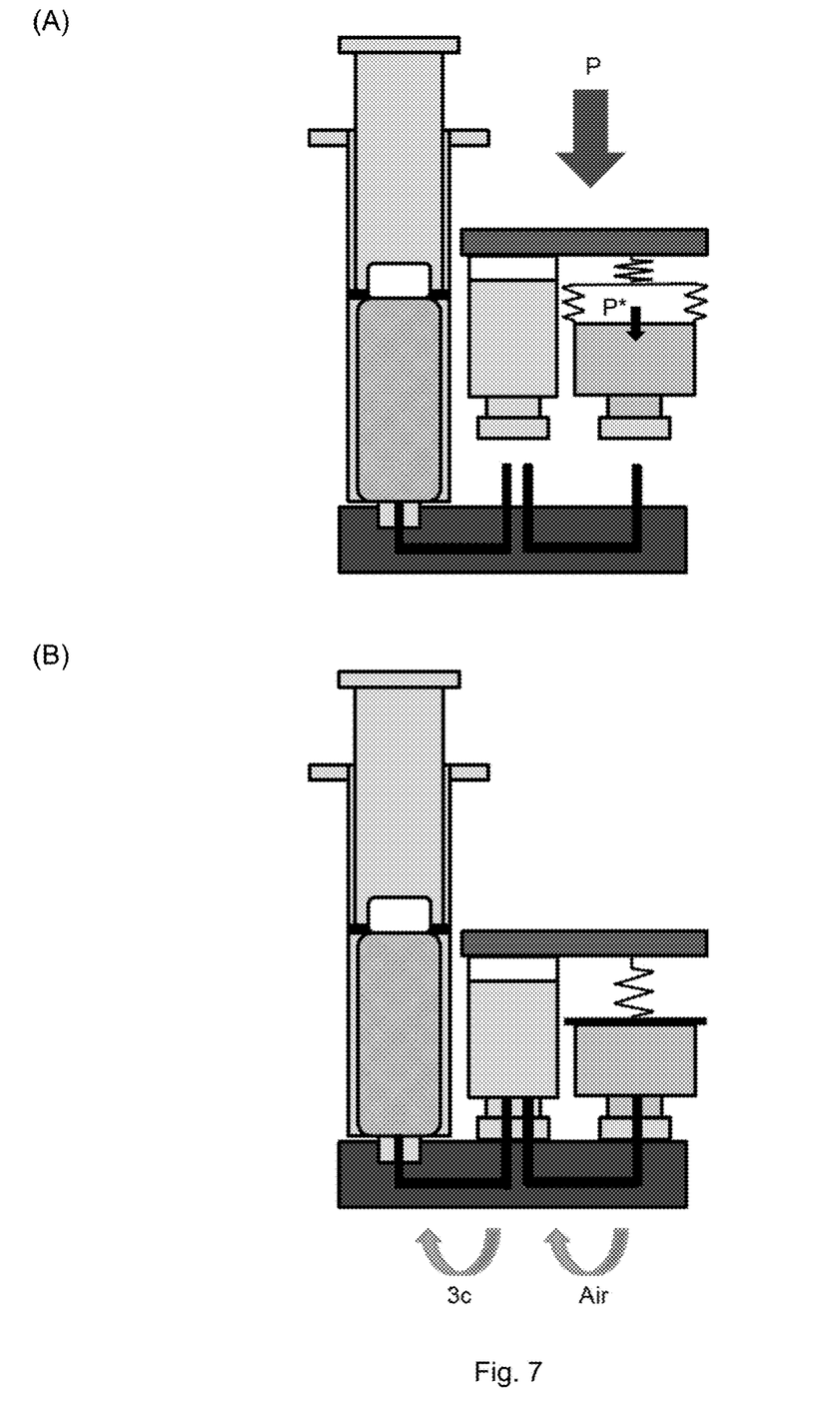

Alternatively, or additionally, the first container may be configured to be pressurizable by a further pressure, as illustrated in FIG. 7. The further pressure is activated after the initiation step of assembling and receiving the containers at the base. The assembly and receival at the base is obtained by applying a manual force. After the containers are received at the base, a further pressure to the first container may be generated manually and/or mechanically by compressing the first container. The compressed volume of the first container, results in pressurized first container, and a positive pressure of the first container.

FIG. 7 shows an embodiment of the device according to the present disclosure for reconstituting a bioactive agent and forming a flowable paste in a syringe, where the first container is pressurized by a further pressure, indicated as P*. (A) shows the configuration before the first and second containers are received at the base, and the connections to the base conduits are formed. (B) shows the configuration when the first and second containers are received at the base and the connections to the conduits are formed.

When the containers are received at the base by applying a manual force (shown as P in FIG. 7), a further pressure (P*) may be generated by an elastic compression and deformation of the first container. The deformation consequently results in a positive pressure in the container. The elastic deformation may be obtained if the container is collapsable, for example by having an accordion-shaped portion as illustrated in FIG. 7. The elastic deformation of the container, and thus the volume of the container, may further be controlled by including an elastic element, such as a spring through which the further pressure is transferred to the first container. The presence of an elastic element contributes to a controllable and reproducible positive pressure.

Pressure

The positive pressure of the first container facilitates turbulent flow and the mixing of the components. Thus, the distribution of the components within the paste, and the time for producing the paste, will depend on the size of the positive pressure.

A positive and variable pressure in a liquid container may be obtained by pressurizing the liquid, for example by an air pressure, or by elastically deforming the container to compress the container volume. However, the higher the pressure, the more costly and the higher the mechanical requirements to the container and the device. It was found that sufficient mixing and a fast formation of the paste may be obtained using a pressure of between 0.1-5 bar.

In an embodiment of the disclosure, the first container is pressurized to between 0.1-5 bar, more preferably between 1-3 bar, and most preferably about 1 bar. In a further embodiment, the first container is pressurized by liquid pressure. In a further embodiment, the liquid is a pressurized liquid.

In another and further embodiment, the first container is pressurized by compression, and optionally elastic deformation. In a further embodiment, the first container comprises a collapsable first container, and/or an elastic element, such as a spring, adapted to compress the volume of the first container.

Figure 5:
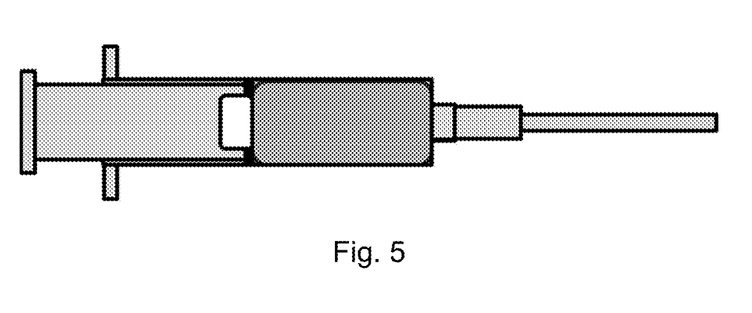

The syringe including the flowable paste may subsequently be detached from the base, and the paste applied at a target site as illustrated in FIG. 5. To ensure fast, easy, and reliable attachment and detachment of the syringe, the syringe is advantageously attached by detachable fastening means, or detachably attached to the base by a locking mechanism. Examples of detachable fastening means include a screw, click-on, slide-on, or snap-fit mechanism.

In an embodiment of the disclosure, the syringe is detachably attached to the base by a locking mechanism, such as a screw, click-on, or slide-on locking mechanism.

The second container, conduits, and syringe have a fixed volume and are non-compressible elements. Thus, when the positive pressure of the first container is released, a pressure wave is generated which advanced through the device. The pressure wave is therefore the driving force for advancing the liquid phases into the syringe and for mixing the phases.

To ensure that the pressure wave propagates unidirectional within the device, i.e. in a direction going from the first container and into the syringe, the syringe advantageously comprises a pressure controlling element 5b placed in the syringe plunger, as illustrated in FIG. 4. The pressure controlling element advantageously acts as a pressure releasing element, such that a backpressure generated within the syringe may be avoided.

The positive pressure of the first container may be obtained by a gas, such as air. Thus advantageously, the pressure controlling element is a gas filter, having the function of a gas release valve. As illustrated in FIG. 4, the air pressure from the first container travels from the first container, through the device, and is discharged to the surroundings at the syringe piston.

The pressure controlling element further provides the advantage that gasses are not trapped within the syringe, and the risk of delivering detrimental gasses exposed to the patient simultaneously with applying the paste, is avoided. In addition to the gasses from the first container, gasses present in the conduits and the second container and syringe, may be released through a gas filter as illustrated in FIGS. 3-4.

Advantageously, the pressure controlling element is further adapted to filtrate fluids in the gaseous state (also referred to as gaseous fluids), while retaining fluids in the liquid state (also referred to as liquid fluids). Thus, the pressure controlling element will allow the gasses to pass through the filter and to the surroundings, while the liquid phases (i.e. the paste forming material, the reconstituted bioactive agent, and the flowable paste) are maintained within the syringe. An example of a pressure controlling element adapted to filtrate gaseous fluids, and retaining liquid fluids is a filter with variable pore size. For example a filter comprising a hydrophobic material may be configured such that the pore size varies depending on the moisture or water content. Upon exposure to increasing water content, the material expands, and thereby decreases the internal pore size. Thus, as long as the filter is exposed to gases, the gases may pass through the filter. However, when the filter is exposed to a liquid phase, the liquid phase cannot pass through.

In an embodiment of the disclosure, the syringe further comprises a pressure controlling element. In a further embodiment, the pressure controlling element is a filter adapted to filtrate gaseous fluids from liquid fluids. In a further embodiment, the filter comprises a composition adapted to be expandable upon contact with water. In a further embodiment, the filter comprises a hydrophobic material.

It follows from the above description that the device of the present disclosure may be considered to have four configurations. The first configuration is illustrated in FIG. 1, and shows the device before the first and second containers are received at the base. The second configuration is illustrated in FIG. 2 and FIG. 7, and shows the device when the first and second containers are received at the base. The third configuration is illustrated in FIG. 3, and shows the device when the bioactive agent is reconstituted. The fourth configuration is illustrated in FIG. 4, and shows the device when the paste is formed in the syringe. When the first and second containers are received at the base, the transition from the first configuration to the fourth configuration automatically and spontaneously occurs due to the pressure present or generated within the pressurizable first container.

Figure 6:
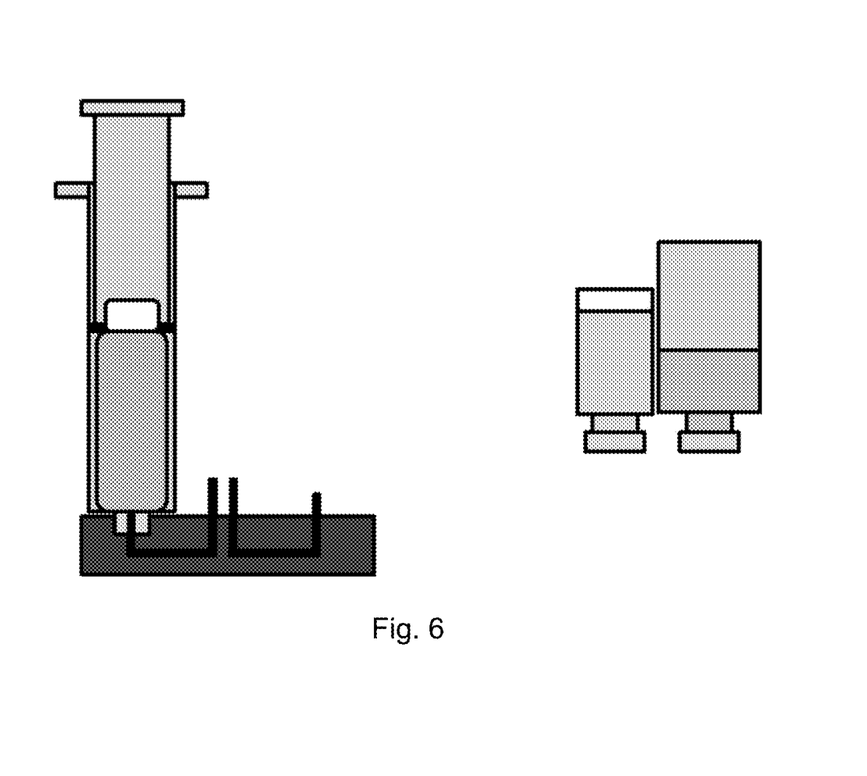

In the first configuration, the first and second containers are mounted in the device, but not received at the base. To minimize the risk of accidental receival at the base, e.g. by an accidental push to the device during storage or transport, the first and second containers are advantageously provided as separate units. An embodiment of the kit of parts is illustrated in FIG. 6. For fast and easy mounting in the device and for easy receival at the base, the first and second containers are advantageously provided as a connected separate unit, as illustrated in FIG. 6.

In an embodiment of the disclosure, the device is provided as a kit of parts comprising a base, a syringe containing a paste forming material, a first container containing a liquid, and a second container containing a bioactive agent. In a further embodiment, the kit comprises a syringe detachably attached to a base, and a first and a second container connected to each other.

Components

The present disclosure provides a fast, easy, and convenient mixing of a liquid, a bioactive agent, and a paste forming material into a paste, such as a flowable paste. The efficiency of the resulting paste will depend on the type of components (i.e. type of liquid, bioactive agent, and paste forming material), the degree of mixing of the components, and the distribution of the components within the paste, as well as the ratio between the components.

Bioactive Agent and Liquid

For the flowable paste to act as a haemostatic matrix, the bioactive agent is advantageously of a type, which acts as a clotting agent, such as thrombin.

Bioactive agents, such as thrombin, are typically expensive and stored in a solid and/or dried state to ensure chemical stability, longer storage times, and thus lower material waste. Advantageously the bioactive agent is a lyophilized agent, such as lyophilized thrombin. Lyophilization, is also known as freeze-drying, and involves dehydration of the bioactive agent, such that it is preserved and stored in a dried solid state. Thus, lyophilization provides an efficient storage form. However, for the lyophilized bioactive agent to be applied by injection, the lyophilized agent must be reconstituted by mixing with a liquid.

It is known in the art that the storage life of injectable substances, such as thrombin, is increased when the substance is stored in a powdered state. Lyophilization is one way of producing a powdered substance from a liquid based material. It involves a rapid freezing of the material at a very low temperature followed by a rapid dehydration by sublimation in a high vacuum.

The resulting lyophilized substance is typically stored in a glass vial or cartridge which is closed by a cap, such as a rubber stopper or septum. It is necessary to reconstitute the powdered or solid substance prior to administration. This is accomplished by mixing the powdered substance with a suitable diluent or liquid.

Further, to ensure sufficient uniform mixing of the bioactive agent within the paste, such that the paste acts as an efficient haemostatic matrix, the bioactive agent is advantageously reconstituted by a liquid capable of dissolving the agent or keeping the agent in essential stable suspension. Further advantageously, the liquid is of a type which acts as a diluent, such that the concentration of the bioactive agent can be easily adjusted. For example, thrombin may be easily dissolved and/or suspended by water, sterile water, saline water, sterile saline, or a mixture of water and glycerol.

In an embodiment of the disclosure, the bioactive agent is a dried or lyophilized substance. In a further embodiment, the bioactive agent comprises thrombin. In a further embodiment, the bioactive agent comprises or consists of lyophilized thrombin.

In one embodiment of the disclosure, the thrombin is recombinant thrombin.

In one embodiment of the disclosure, the thrombin is human thrombin.

In an embodiment of the disclosure, the liquid is a diluent. In a further embodiment, the liquid is an aqueous medium selected from the group of: water, glycerol, sterile water, saline, sterile saline, a calcium chloride solution, a buffered aqueous solution, and combinations thereof.

Thrombin is added to the paste of the present disclosure in an amount sufficient to ensure effective haemostasis of the paste. In one embodiment thrombin will be present at a concentration in the range of about 100 IU/ml paste to about 500 IU/ml paste, such as about 150 IU/ml paste to about 450

IU/ml paste, for example about 200 IU/ml paste to about 400 IU/ml paste, such as about 250 IU/ml paste to about 350 IU/ml paste.

In one embodiment, thrombin will be present in the paste at a concentration in the range of about 50 IU/g paste to about 5000 IU/g paste, preferably between about 100 IU/g paste to about 1000 IU/g paste, such as between about 200 IU/g paste to about 800 IU/g paste.

Reconstitution of a dry preparation of a bioactive agent such as thrombin is traditionally performed using a syringe with a needle to withdraw the diluent from one separate vial and inject it into another separate vial containing the dry thrombin, whereupon the latter vial is shaken or swirled to thoroughly mix the two constituents. The syringe with needle is then used to withdraw from this vial the desired amount of reconstituted bioactive agent. Because two separate containers are used, the person reconstituting the bioactive agent must be certain to mix the correct amounts such that a proper concentration of the mixture results.

In the present disclosure, the components are pre-loaded in the syringe and containers in predefined amounts and ratios. Thus, the steps of measuring the correct amount of the components are avoided, and a predefined amount of paste is rapidly, easily, and conveniently produced.

Paste Forming Material

To ensure the formation of an effective paste, such as a paste with sufficient flowability to be delivered to a target site by a syringe, and such that the delivered paste may be precisely and fixedly positioned at the target site, certain paste forming materials and certain paste compositions (i.e. ratios between the components) were found advantageous.

Advantageously, the paste forming material comprises a biocompatible polymer.

The biocompatible polymer of the present disclosure may be a biologic or a non-biologic polymer. Suitable biologic polymers include proteins, such as gelatine, collagen, albumin, haemoglobin, casein, fibrinogen, fibrin, fibronectin, elastin, keratin, and laminin; or derivatives or combinations thereof. Particularly preferred is the use of gelatine or collagen, more preferably gelatine. Other suitable biologic polymers include polysaccharides, such as glycosaminoglycans, starch derivatives, xylan, cellulose derivatives, hemicellulose derivatives, agarose, alginate, and chitosan; or derivatives or combinations thereof. Suitable non-biologic polymers will be selected to be degradable by either of two mechanisms, i.e. (1) break down of the polymeric backbone or (2) degradation of side chains which result in aqueous solubility. Exemplary nonbiologic polymers include synthetics, such as polyacrylates, polymethacrylates, polyacrylamides, polyvinyl resins, polylactide-glycolides, polycaprolactones, and polyoxyethylenes; or derivatives or combinations thereof. Also combinations of different kinds of polymers are possible.

In one embodiment, the biocompatible polymer is biologically absorbable. Examples of suitable biologically absorbable materials include gelatine, collagen, chitin, chitosan, alginate, cellulose, oxidised cellulose, polyglycolic acid, polyacetic acid and combinations thereof. It will be understood that various forms thereof, such as linear or cross-linked forms, salts, esters and the like are also contemplated for the present disclosure. In a preferred embodiment of the invention, the biologically absorbable material is gelatine. Gelatine is preferred since gelatine is highly biologically absorbable. Furthermore, gelatine is highly biocompatible, meaning that it is non-toxic to an animal, such as a human being, when/if entering the blood stream or being in long-term contact with human tissues.

The gelatine typically originates from a porcine source, but may originate from other animal sources, such as from bovine or fish sources. The gelatine may also be synthetically made, i.e. made by recombinant means.

In a preferred embodiment the biocompatible polymer is cross-linked. Cross-linking usually renders the polymer substantially insoluble in an aqueous medium. In one embodiment, the biocompatible polymer consists of powder particles which are substantially insoluble in an aqueous medium. Any suitable cross-linking methods known to a person of skill may be used including both chemical and physical cross-linking methods.

In an embodiment of the disclosure, the paste forming material comprises water-insoluble particles and/or cross-linked particles. In a further embodiment, the paste forming material comprises cross-linked gelatine particles.

The cross-linked powder particles are in one embodiment less than approximately 1000 microns in size, i.e. so that they are able to pass through a 1×1 mm sieve.

Generally at least 90% of the powder particles have a diameter of between 1 µm and 1200 µm.

In one embodiment, the average particle diameter is between 1 µm and 1000 µm, such as between 10 µm and 800 µm, for example between 50 µm and 600 µm, such as between 100 µm and 500 µm, for example between 200 µm and 400 µm, such as about 300 µm.

In some applications it is desirable to have a smaller particle size, whereby a smoother paste can be obtained. Thus in one embodiment, the average particle diameter is less than 100 µm, such as less than 50 µm, for example less than 30 µm, such as less than 20 µm, for example less than 10 µm. One example of an application where a smoother paste is desirable is in the control of bone bleeding.

Particles of a certain size distribution can be achieved by passing a powdered composition through one or more sieves having a certain mesh size and collecting the powder which passes through and/or is retained by a certain mesh size. For example, powder particles having a size distribution between approximately 200 µm and 1000 µm can be obtained by collecting the powder which is able to pass through a 1×1 mm sieve but is retained by a 0.2×0.2 mm sieve.

In one embodiment, the paste forming material comprises or consists of cross-linked gelatine particles obtained from a micronized porous gelatine sponge, which has been cross-linked by dry heat treatment.

To further facilitate fast formation of the paste, and fast and uniform mixing between the paste forming material and the reconstituted bioactive agent, it was found advantageously that the paste forming material is in the form of a solid, such as a dry composition, dried paste, or a powder. Further advantageously, the powder may be pressed powder, and shaped into a pellet. Pressed powders or pellets are easily pre-loaded into a syringe, and provides a fixed dosage. Thus, careful measurement of amounts of paste forming material is avoided. The paste forming material may also be provided as a vacuum expanded dry paste, having a density between about 1 mg/ml to about 40 mg/ml.

In an embodiment of the disclosure, the paste forming material is in the form of a solid, such as a dry composition. In a further embodiment, the paste forming material is a dried paste, such as a lyophilized paste. In another and further embodiment, the paste forming material is in the form of a powder, or pressed powder. In another embodiment, the paste forming material has a density between about 1 mg/ml to about 40 mg/ml, such as between 5 mg/ml to about 35 mg/ml, for example between about 10 mg/ml to about 35 mg/ml.

Advantageously, the components are pre-loaded in the syringe and containers in predefined amounts and ratios. Thus, measurements of component amounts are avoided, and a predefined amount or volume of paste is rapidly, easily, and conveniently produced.

In an embodiment of the disclosure, the volume of paste formed in the syringe is between 1-15 ml, more preferably between 6-12 ml, and most preferably between 7-10 ml, such as 8 ml.

It was found that the present disclosure may provide pastes that act as a haemostatic matrix, and further are especially efficient as haemostatic matrix due to the composition, flowability, and rheology.

In an embodiment of the disclosure, the paste is a haemostatic paste.

Preferably, the paste formed is a flowable paste.

Base Receival

In the first configuration shown in FIG. 1, the first and second containers are mounted in the device, but not received at the base. In the second configuration shown in FIG. 2 and FIG. 7, the first and second containers are received at the base, and the connections to the conduits of the base are formed. Advantageously, the receival of the first and second container at the base occurs simultaneously and such that the connection to conduits is formed essentially instantly, thereby reducing the risk of spillage and wasted drug and other materials.

Instant connection upon receival at the base may be obtained if the two containers each have a sealed opening. A sealed opening may be connected instantly by e.g. piercing or penetration. Thus advantageously, the seals are adapted to be pierced or penetrated.

The two sealed openings may be connected and pierced simultaneously by a manual push towards the base station, as illustrated in FIG. 2. Upon piercing the sealing, the connection to the container is created.

In an embodiment of the disclosure, the first container has a first sealed opening, and the second container has a second sealed opening, and wherein the openings are configured to be received at the base. In a further embodiment, the seals are adapted to be pierced.

To further facilitate simultaneous piercing of the first sealed opening and the second sealed opening, the first and second containers are advantageously attached to each other such that the sealed openings are in the same plane as illustrated in FIGS. 1 and 6.

In an embodiment of the disclosure, the first and second containers are attached to each other, such that the sealed openings are in the same plane.

Advantageously, the conduits, or tubing, of the base are configured to pierce the sealing of the containers, when the mounted containers are pushed into receival at the base. Thus, fast, instant, and reliable receival at the base is obtained by applying a manual pressure (P) as illustrated in FIG. 2.

In an embodiment of the disclosure, the first and second containers are configured to be received at the base by applying a pressure, such as a manual pressure.

To further enable simultaneous piercing of the first sealed opening and the second sealed opening, it is advantageous that the first conduit and the second conduit have at least a portion extending perpendicular to the plane of the base, which is configured for piercing the seals. The portions may be configured for piercing by having a pointed end for penetrating the sealed openings, such as a needle shaped end. FIG. 1 shows an embodiment, where the first conduit has at least one end 6a configured for piercing a sealed opening, and the second conduit has at least one end 6b configured for piercing a sealed opening. Optionally both ends of the conduit may be configured for piercing sealed opening.

In an embodiment of the disclosure, the first conduit and the second conduit have at least one portion extending perpendicular to the plane of the base. In a further embodiment, the at least one perpendicular portion of the conduits comprises a pointed end configured for penetrating the sealed openings of the containers. In a further embodiment, the perpendicular portion of the conduits has a needle shape.

To minimize the risk of spillage and wasted drug and other materials, it may be advantageous that the second container is received at the base immediately before the first container is received. Thus, the connection to the second conduit is formed immediately before the connection to the first conduit, which ensures that the pressure driven force is not introduced into the device before all connections are formed.

Receival of the second container at the base immediately before the first container may be obtained if a perpendicular portion of the first conduit is shorter than a perpendicular portion of the second conduit, as illustrated in FIG. 1.

In an embodiment of the disclosure, the perpendicular portion of the first conduit is shorter than the perpendicular portion of the second conduit.

To obtain a compact device, and for easy and convenient receival of the containers at the base, the first conduit and the second conduit advantageously each form a U-shaped tubing. An embodiment of a base comprising U-shaped conduits is illustrated in FIG. 1.

The first conduit forms a U, where the first end of the tube is connected to the first container and the second end of the tube is connected to the second container. To minimize the risk of spillage and wasted bioactive material and other materials, the second end of the tube is advantageously slightly longer than the first end of the tube. Thus, the second end of the tube may pierce the sealing of the of the second container, immediately before the first end of the tube pierces the sealing of the first container.

The second conduit also forms a U, where the first end of the tubing is connected to the second container, and the second end is connected to the syringe. For easy receival of the second container at the base, the first end of the tubing has advantageously the same length as the second end of first conduit, as illustrated in FIG. 1.

Items

The presently disclosed may be described in further detail with reference to the following items.

1. A device (1) for reconstituting a bioactive agent and forming a paste, the device comprising:
   a base (2) configured for receiving:
      a first container (3) containing a liquid (3a), and
      a second container (4) containing the bioactive agent (4a),
   a syringe (5) containing a paste forming material (5a), the syringe being attachable to the base,
   wherein the base has a first conduit (6) for fluidly connecting the first container with the second container and a second conduit (7) for fluidly connecting the second container with the syringe, and
   wherein the first container is configured to be pressurizable such that when the first and second containers are received at the base, the liquid is forced through the first conduit into the second container, thereby reconstituting the bioactive agent, and the reconstituted bioactive agent is forced through the second conduit into the syringe, such that a paste (5c) is formed.

2. The device according to item 1, wherein the paste forming material comprises a biocompatible polymer.

3. The device according to any of the preceding items, wherein the paste forming material comprises water-insoluble particles and/or cross-linked particles.

4. The device according to any of the preceding items, wherein the paste forming material comprises cross-linked gelatine particles.

5. The device according to any of the preceding items, wherein the paste forming material is in the form of a solid, such as a dry composition.

6. The device according to any of the preceding items, wherein the paste forming material is a dried paste, such as a lyophilized paste.

7 The device according to any of the preceding items, wherein the paste forming material is in the form of a powder, or pressed powder.

8. The device according to any of the preceding items, wherein the paste forming material has a density between about 1 mg/ml to about 40 mg/ml, such as between 5 mg/ml to about 35 mg/ml, for example between about 10 mg/ml to about 35 mg/ml.

9. The device according to any of the preceding items, wherein the bioactive agent is a dried or lyophilized substance.

10. The device according to any of the preceding items, wherein the bioactive agent comprises thrombin.

11. The device according to any of the preceding items, wherein the bioactive agent comprises or consists of lyophilized thrombin.

12. The device according to any of the preceding items, wherein the liquid is a diluent.

13. The device according to any of the preceding items, wherein the liquid is an aqueous medium selected from the group of: water, glycerol, sterile water, saline, sterile saline, a calcium chloride solution, a buffered aqueous solution, and combinations thereof.

14. The device according to any of the preceding items, wherein the first container is pressurized to between 0.1-5 bar, more preferably between 1-3 bar, and most preferably about 1 bar.

15. The device according to any of the preceding items, wherein the first container is pressurized by liquid pressure.

16. The device according to item 15, wherein the liquid is a pressurized liquid.

17. The device according to any of the preceding items, wherein the first container is pressurized by compression, optionally elastic deformation.

18. The device according to item 17, comprising a collapsable first container, and/or an elastic element, such as a spring, adapted to control the volume of the first container.

19. The device according to any of the preceding items, wherein the paste is a haemostatic paste.

20. The device according to any of the preceding items, wherein the paste is flowable.

21. The device according to any of the preceding items, wherein the volume of paste formed in the syringe is between 1-15 ml, more preferably between 6-12 ml, and most preferably between 7-10 ml, such as 8 ml.

22. The device according to any of the preceding items, wherein the syringe is detachably attached to the base by a locking mechanism, such as a screw, click-on, slide-on, or snap-fit locking mechanism.

23. The device according to any of the preceding items, wherein the syringe further comprises a pressure controlling element.

24. The device according to item 23, wherein the pressure controlling element is a filter adapted to filtrate fluids in the gaseous state from fluids in the liquid state.

25. The device according to item 24, wherein the filter comprises a composition adapted to be expandable upon contact with water.

26. The device according to any of items 24-25, wherein the filter comprises a hydrophobic material.

27. The device according to any of the preceding items, wherein the first container has a first sealed opening, and the second container has a second sealed opening, and wherein the openings are configured to be received at the base.

28. The device according to item 27, wherein the seals are adapted to be pierced.

29. The device according to any of the preceding items, wherein the first and second container are attached to each other, such that the sealed openings are in the same plane.

30. The device according to any of the preceding items, wherein the first conduit and the second conduit have at least one portion extending perpendicular to the plane of the base.

31. The device according to item 30, wherein the at least one perpendicular portion of the conduits comprises a pointed end configured for penetrating the sealed openings of the containers.

32. The device according to item 31, wherein the perpendicular portion of the conduits has a needle shape.

33. The device according to any of items 30-32, wherein the perpendicular portion of the first conduit is shorter than the perpendicular portion of the second conduit.

34. The device according to any of the preceding items, wherein the first and second containers are configured to be received at the base by applying a manual pressure.

35. A kit of parts for the device according to any of items 1-34, comprising a base, a syringe containing a paste forming material, a first container containing a liquid, and a second container containing a bioactive agent.

36. A method for reconstituting a bioactive agent and forming a paste, the method comprising:
providing a first container (3) containing a liquid (3a) under positive pressure,
providing a second container (4) containing the bioactive agent (4a),
providing a syringe (5) containing a paste forming material (5a), and
fluidly connecting the first container with the second container (6) and fluidly connecting the second container with the syringe (7) such that the liquid is forced from the first container into the second container, thereby reconstituting the bioactive agent, and the reconstituted bioactive agent is forced from the second container into the syringe, such that a paste (5c) is formed.

37. The method according to item 36, configured to be carried out using the device according to any of items 1-34 or the kit of parts according to item 35.

38. Use of the device according to any of items 1-34 or the kit of parts according to item 35 for the method according to item 36.

REFERENCE NUMBERS

1—device
2—base
3—first container
3a—first container liquid
3b—first container opening
4—second container
4a—second container bioactive agent
4b—second container opening
4c—reconstituted bioactive agent
5—syringe
5a—syringe paste forming material
5b—filter
5c—paste
6—first conduit
6a—first conduit end
7—second conduit
7a—second conduit end

REFERENCES

[1] WO 10/043685.

What is claimed is:

1. A device for reconstituting a bioactive agent and forming a paste, the device comprising:
   a first container containing a liquid,
   a second container containing the bioactive agent,
   a base configured for receiving the first and second container,
   a syringe containing a paste forming material, the syringe being attachable to the base,
   wherein the base has a first conduit for fluidly connecting the first container with the second container and a second conduit for fluidly connecting the second container with the syringe, so that application of pressure to the liquid in the first container
   a) forces the liquid from the first container through the first conduit into the second container, thereby reconstituting the bioactive agent, and
   b) forces the reconstituted bioactive agent through the second conduit into the syringe, such that a paste is formed,
   wheren the first container is pressurized by compression.

2. The device according to claim 1, wherein the paste forming material comprises a biocompatible polymer.

3. The device according to claim 1, wherein the bioactive agent is a dried or lyophilized substance.

4. The device according to claim 1, wherein the liquid is a diluent.

5. The device according to claim 1, wherein the pressure to the liquid in the first container for forcing the liquid from the first container through the first conduit into the second container and for forcing the reconstituted bioactive agent through the second conduit into the syringe is between 0.1-5 bar.

6. The device according to claim 1, wherein the pressure of the first container is obtained by gas pressurizing the liquid.

7. The device according to claim 1, comprising a collapsible first container, and/or an elastic element, element adapted to control the volume of the first container.

8. The device according to claim 7, wherein the elastic element is as spring adapted to control the volume of the first container.

9. The device according to claim 1, wherein the paste is a haemostatic paste.

10. The device according to claim 1, wherein the syringe further comprises a pressure controlling element.

11. The device according to claim 10, wherein the pressure controlling element is a filter adapted to filtrate fluids in the gaseous state from fluids in the liquid state.

12. The device according to claim 1, wherein the first container has a first sealed opening, and the second container has a second sealed opening, and wherein the openings are configured to be received at the base.

13. The device according to claim 12, wherein the first and second container are attached to each other, such that the first and second sealed openings are at the same level.

14. The device according to claim 1, wherein the first container is pressurized by elastic deformation.

15. The device according to claim 1, wherein the applied pressure on the liquid in the first container is between 1-3 bar or about 1 bar.

16. The device according to claim 1, wherein the first conduit and the second conduit have at least one portion extending perpendicular to a plane of the base.

17. A kit of parts for the device according to claim 1, comprising the base, the syringe containing a paste forming material, the first container containing a liquid, and the second container containing a bioactive agent.

18. A method for reconstituting a bioactive agent and forming a paste, the method comprising:
   providing a first container containing a liquid;
   providing a second container containing the bioactive agent;
   providing a syringe containing a paste forming material;
   fluidly connecting the first container with the second container and fluidly connecting the second container with the syringe; and
   finally applying pressure to the liquid in the first container such that the liquid is forced from the first container into the second container, thereby reconstituting the bioactive agent, and the reconstituted bioactive agent is forced from the second container into the syringe, such that a paste is formed.

* * * * *